United States Patent [19]

Kondo et al.

[11] 4,313,014
[45] Jan. 26, 1982

[54] PROCESS FOR THE SEPARATION OF CYCLOHEXENE

[75] Inventors: Tsuneyuki Kondo, Konan; Kishio Miwa, Kamakura; Takehisa Inoue, Tokyo, all of Japan

[73] Assignee: Toray Industries Incorporated, Tokyo, Japan

[21] Appl. No.: 181,820

[22] Filed: Aug. 27, 1980

[51] Int. Cl.³ .............................................. C07C 7/13
[52] U.S. Cl. .................................. 585/827; 208/310 Z
[58] Field of Search ...................... 585/827; 208/310 Z

[56] References Cited

U.S. PATENT DOCUMENTS

| | | | |
|---|---|---|---|
| 4,014,949 | 3/1977 | Hedge | 208/310 Z |
| 4,069,172 | 1/1978 | Kanaoka et al. | 585/827 |
| 4,159,284 | 6/1979 | Seko et al. | 208/310 Z |

*Primary Examiner*—Jacqueline V. Howard
*Attorney, Agent, or Firm*—Scully, Scott, Murphy & Presser

[57] ABSTRACT

In the separation of cyclohexene from a feed which contains cyclohexene and cyclohexane, the feed is contacted with a type X and/or type Y aluminosilicate zeolite, thereby adsorbing cyclohexene selectively on the zeolite, and then the zeolite which adsorbed cyclohexene is contacted with a trimethylbenzene to desorb cyclohexene.

8 Claims, 1 Drawing Figure

PROCESS FOR THE SEPARATION OF CYCLOHEXENE

BACKGROUND OF THE INVENTION

This invention relates to a process for the separation of cyclohexene and more particularly to a process for separating cyclohexene from a feed which contains a mixture of cyclohexene and cyclohexane, selectively by adsorptive separation techniques.

Cyclohexene is one of cyclic unsaturated hydrocarbons useful as starting materials for manufacture of organic compounds such as cyclohexanol and adipic acid. Generally, cyclohexene is prepared by a selective partial hydrogenation of benzene or a selective dehydrogenation or oxidative dehydrogenation of cyclohexane. In this case, the reaction product is obtained as a mixture (hereinafter referred to simply as the "reaction mixture") containing benzene, cyclohexene, and cyclohexane. Therefore, in order to obtain cyclohexene advantageously on an industrial scale, the separating and purifying operation for the reaction mixture is important. There has been proposed a method of separating, by the adsorption technique, cyclohexene from the reaction mixture after separation of benzene, namely a mixture scarcely containing benzene and consisting essentially of cyclohexene and cyclohexane. This method employs zeolite as an adsorbent and also employs as a displacer or developer at least one member selected from the group consisting of olefinic hydrocarbons, halogenated aliphatic hydrocarbons, ethers and carbon disulfide (see Japanese Published Unexamined Patent Application No. 64530/1980).

According to this method, however, the displacer or developer deteriorates easily because it is chemically unstable, so it is unpreferrable to reuse it by recycle. Therefore it is difficult to employ as an industrial method. Besides, such deterioration of the displacer or developer causes degradation of the adsorptive capability of the adsorbent, so that it becomes impossible to separate cyclohexene in sufficiently high purity. Furthermore, a regenerative treatment is often required to recover the adsorptive capability of the adsorbent, and this has been an operational problem. When low boiling compounds are used as the displacer or developer, a special care is required in handling it and the working efficiency slows down.

It is an object of this invention to provide a new desorbent for cyclohexene which is chemically stable and does not deteriorate, and which can be easily and effectively separated from the mixture of cyclohexene and the desorbent with a distillation method.

It is another object of this invention to provide an effective industrial process for the separation of cyclohexene.

It is a further object of this invention to provide a process for the separation of cyclohexene whereby cyclohexene can be separated in high purity without deterioration in the performance of an adsorbent.

It is a still further object of this invention to provide a part of the method of separating and recovering each component from the reaction mixture which is obtained by a manufacturing method for cyclohexene.

Other objects and advantages of this invention will become apparent from the following description.

SUMMARY OF THE INVENTION

The foregoing objects of this invention are achieved by a process for the separation of cyclohexene which process comprises the steps of contacting a feed which contains a mixture of cyclohexene and cyclohexane with a type X and/or type Y aluminosilicate zeolite to allow cyclohexene to be selectively adsorbed on the zeolite, and contacting the cyclohexene-adsorbed zeolite with at least one of trimethylbenzenes to allow cyclohexene to be desorbed therefrom.

The foregoing and other objects are effectively achieved by providing a process for the separation of cyclohexene comprising the steps of:

(a) contacting a feed which contains a mixture of cyclohexene and cyclohexane with a type X and/or type Y aluminosilicate zeolite adsorbent, whereby a greater percentage of cyclohexene than other components of said feed is adsorbed on said adsorbent;

(b) contacting said adsorbent with a desorbent which contains at least one of trimethylbenzenes, whereby cyclohexene is desorbed therefrom; and (c) re-using in step (a) said adsorbent which desorbed cyclohexene and adsorbed trimethylbenzene.

BRIEF DESCRIPTION OF THE DRAWING

The drawing represents a schematic arrangement and flow diagram illustrating one specific embodiment of this invention, showing a fixed bed apparatus connected for countercurrent flow operations. This drawing is intended to be illustrative, and not to define or to limit the scope of the invention, which is defined in the claims.

DESCRIPTION OF THE PREFERRED EMBODIMENT

Figure 1:
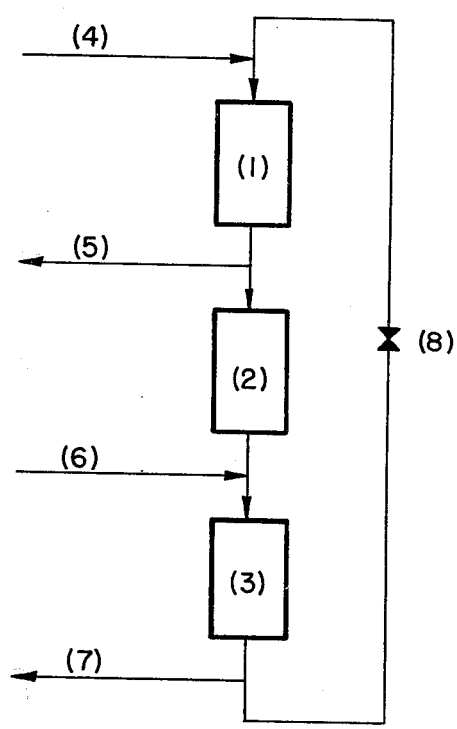

The feed which contains a mixture of cyclohexene and cyclohexane and which is to be subjected to the separation in the invention, is one after removal of benzene as much as possible in known manner from the reaction mixture. The reaction mixture as used herein is mainly the reaction product obtained in the preparation of cyclohexene by, in general, a selective hydrogenation of benzene or a selective dehydrogenation or oxidative dehydrogenation of cyclohexane. Therefore, the composition of each component of the reaction mixture is optional. Furthermore, although this differs according to the kink of producing method for cyclohexene, there may be contained small amounts of side reaction products, for example, unsaturated hydrocarbons such as 1,3-cyclohexadiene, 1,4-cyclohexadiene, and methylcyclopentene, and other hydrocarbons.

When the above reaction mixture contains a lot of water, it is divided in two layers. It is preferred to separate the reaction mixture from the water layer with an usual method. It is advantageous that water dissolved in the reaction mixture is removed by some suitable means. For example, water can be separated and removed by distillation, or by using a zeolite (e.g. the type A synthetic aluminosilicate zeolite manufactured by Union Carbide Corp., U.S.) whichhas substantially no adsorbing capability for any of benzene, cyclohexane and cyclohexene, in the latter case water alone is adsorbed and removed. Any known methods may be used for the separation of benzene from such a reaction mixture. Preferably, benzene is extractively separated using a suitable extracting reagent, or is separatively removed by adsorptive separation. And the mixture from which benzene has been removed in such a manner, is employable in the process of this invention. The feed used in the process of this invention may be of any composition. Furthermore, although this differs according to the kind of producing method for cyclohexene and that of separating method for benzene, there may be contained small amounts of unsaturated hydrocarbons such as benzene, 1,3-cyclohexadiene, 1,4-cyclohexadiene, and methylcyclopentane, and other hydrocarbons. When the adsorbent is continuously recycled small amounts of trimethylbenzenes may also be contained. The amount of benzene contained in the aforesaid feed is preferably not larger than 5% and more preferably not larger than 1%. If benzene is contained above 5%, it will become difficult to separate cyclohexene efficiently because the adsorbent also adsorbs benzene.

Type X aluminosilicate zeolites used in the invention indicate zeolites which possess a similar crystal structure to that of faujasite, and are a kind of well-known zeolites approximated by the following formula

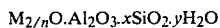

$M_{2/n}O.Al_2O_3.xSiO_2.yH_2O$

M: metal
n: valence of M
x: a number of 2 to 3
y: content of water of crystallization There may be used any type X aluminosilicate zeolites which have been prepared in known manner.

Type Y aluminosilicate zeolites used in the invention indicate zeolites possessing a similar crystal structure to that of faujasite, and are a kind of well-known zeolites approximated by the following formula

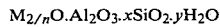

$M_{2/n}O.Al_2O_3.xSiO_2.yH_2O$

M: metal
n: valence of M
x: a number of 3 to 6
y: content of water of crystallization Any type Y aluminosilicate zeolites prepared in known manner are employable. Type X and type Y aluminosilicate zeolites may be used alone or as a mixture in any desired ratio.

As the metal which constitutes type X and/or type Y aluminosilicate zeolites, any metals may be used. This metal usually can be exchanged as cations. Preferably used are alkali metals, particularly sodium and potassium are preferred. Metal ions may be substituted partially or wholly by hydrogen ion or ammonium ion. Also, metal ions may be ion-exchanged with two or more metals. The ion-exchange may be carried out using any known techniques, and the ion-exchange amount is optional. For example, a water-soluble metallic salt is dissolved in water and this solution is contacted with zeolite to allow ion-exchange to take place. Examples of such a water-soluble metallic salt are chlorides, nitrates and sulfates. Although the concentration of the solution differs according to the kind of metallic salts, about 1 to about 10 wt. % is preferred. Either a batch type or flow type may be adopted for the ion exchange. Ion-exchange temperatures usually employed are in the range of 20° to 100° C., but in order to increase the ion-exchange rate, temperatures of 50° to 100° C. are preferred. The ion-exchange amount, although this differs according to the kind of ion, may be set to any desired values, depending on the solution concentration and the ion-exchange temperature. After the ion-exchange treatment, the zeolite used should be thoroughly washed with water until, for example, chloride ion $(Cl^-)$ or nitrate ion $(NO_3^-)$ is no longer detected.

Before using type X and/or type Y aluminosilicate zeolites as adsorbents, their water of crystallization must be removed in advance. Usually, the content of water of crystallization is reduced by heating at a temperature not lower than 100° C. Preferably a heating at 200° C. to 700° C. can remove most of water. If the heating is performed at a temperature below 100° C., there will be removed only a part of the water resulting in decrease in the adsorption amount of cyclohexene etc. On the other hand, heating at a temperature above 700° C. can cause breakage of the cyrstal structure of type X and/or type Y aluminosilicate zeolites, so that the adsorption amount of cyclohexene etc. becomes decreased.

The type X and/or type Y aluminosilicate zeolites used in the invention may assume any shapes, including powdered and disintegrated forms, further they may be in the form of moulded particles obtained using extruder, granulator, pelletizer, and so on. Usually, a binder is used for the moulding. But if satisfactory mouldings are obtainable even without using a binder, the use of a binder may be omitted. As the binder there may be employed, for example, alumina, silica, potter's clay, and acid clay.

The desorbent as referred to herein has the ability of expelling cyclohexene which is selectively adsorbed on type X and/or type Y aluminosilicate zeolite in the desorbing operation, and the desorbent, which has displaced cyclohexane by expelling the latter from the adsorbent and is now adsorbed on the adsorbent, also has the ability of being expelled from the adsorbent surface by the next adsorbing operation. Thus the desorbent is capable of being used continuously in a recycled manner. Further, the desorbent is capable of being easily separated from a solution containing cyclohexene or cyclohexane by a usual method.

The desorbent used in this invention comprises at least one of trimethylbenzenes. Preferably used are 1,2,3-trimethylbenzene and 1,3,5-trimethylbenzene, of which the latter is used most preferably.

The desorbent may be used alone or as a mixture of trimethylbenzenes. Also, the desorbent used in the invention may be in a mixed state with other compound. In this case, other compounds to be mixed with the desorbent are not limited at all. For example, the desorbent may be diluted with paraffins or cycloparaffins other than cyclohexane.

The temperature in the adsorbing operation is in the range of from 0° C. to 300° C., preferably from room temperature to 200° C., and the pressure from atmospheric pressure to 40 kg/cm², preferably from nearly atmospheric pressure to 30 kg/cm². The adsorbing operation may be carried out either in liquid phase or gas phase. In order to lower the adsorbing temperature, liquid phase is preferred.

In this invention, the adsorptive separation of cyclohexene from the foregoing feed involves basic two steps of a selective adsorption step and a desorption step. It is preferable that these two steps be repeated continuously. Generally, in the adsorption step a feed containing a mixture of cyclohexane and cyclohexene is contacted with an adsorbent which has adsorbed a desorbent, whereby cyclohexene is adsorbed on the adsorbent while it expels the desorbent. Therefore, the raffinate thereof consists of a solution which contains mainly the desorbent and cyclohexane. Cyclohexane is separated and recovered from the desorbent by distillation (by utilization of the difference in boiling point), while the desorbent is recycled. In the next desorption step, the adsorbent which has adsorbed cyclohexene in the adsorption step is contacted with a desorbent whereby the desorbent is adsorbed on the adsorbent while it expels cyclohexene. Consequently, the extract thereof consists principally of cyclohexene and the desorbent. The two are also separated and recovered by distillation. The adsorbent with the desorbent adsorbed thereon can be re-used as an adsorbent in the adsorption step. In this case, cyclohexene is adsorbed while it expels the desorbent. Cyclohexene as product is utilized in various uses, while the desorbent is recycled.

Working examples of this invention are given below to explain the effect of the invention in detail, but the invention is not limited thereto.

In working examples, the performance of type X and/or type Y aluminosilicate zeolites and that of the desorbent will be expressed in terms of a selective adsorption coefficient, $\alpha$, which is defined by the following formulae: t,0090

Where, HX is cyclohexene, CX is cyclohexane, and A is a desorbent.

It is preferable that the selective adsorption coefficient of cyclohexene and cyclohexene, $\alpha HX/CX$, is as high as possible. At a low $\alpha HX/CX$, a large amount of adsorbent is required for the adsorptive separation of cyclohexene; besides, the recovery of cyclohexene per unit adsorbent is reduced so the energy cost is increased, which is uneconomical.

On the other hand, the selective adsorption coefficient of cyclohexene and desorbent, $\alpha HX/A$, is preferably close to the unity. When $\alpha HX/A$ is too large, a large amount of the desorbent A is required for the desorption of cyclohexene adsorbed on the adsorbent. Conversely, when $\alpha HX/A$ is too small, it is disadvantage tht cyclohexene is not adsorbed to a satisfactory extent so the separation efficiency from cyclohexane decrease. In general, the value of $\alpha HX/A$ differ according to the adsorption conditions (adsorption temperature, the composition of the foregoing feed, etc.). When the value of $\alpha HX/CX$ is sufficiently large, there the range of $\alpha HX/A$ is not limited. Thus the range of employable value of $\alpha HX/A$ is affected by the value of $\alpha HX/CX$. Therefore, it is practically difficult to define the range of value of $\alpha HX/A$, but a preferred range is 0.1 to 10, more preferably 0.2 to 5, and particularly the range of 0.8 to 3 is used preferably.

EXAMPLE 1

As an adsorbent a commercially available synthetic type X aluminosilicate zeolite (Molecular Sieve 13X, a product of Union Carbide; metal cation is Na+) was calcined for 2 hours in the air at 450° C. and then allowed to stand in a phosphorus pentoxide desiccator. The adsorbent (2 g.) was used which was 14 to 24 mesh in size. The adsorbent was mixed with 2 g. of a liquid mixture consisting of cyclohexene, cyclohexane, normal decane as a diluent, and 1,3,5-trimethylbenzene as a desorbent, and the resulting mixture was allowed to stand for 1 hour at 80° C. at a pressure of about 2 kg/cm² with stirring at times. The composition of the liquid mixture was cyclohexene:cyclohexane:normal decane:1,3,5-trimethylbenzene=1:1:1:3 (weight ratio). The change in composition of the liquid mixture before and after adsorption was determined with a gas chromatography, when the substantially unadsorbed normal decane was used as a standard substance. $\alpha HX/CX$ and $\alpha HX/A$ (A: 1,3,5-trimethylbenzene) was found to be 7.1 and 0.98, respectively. Any high boiling compounds were not detected with gas chromatography. The colour of adsorbent (white) was not changed.

EXAMPLE 2

The same procedure as in Example 1 was repeated except that 1,2,4-trimethylbenzene was used as the desorbent. $\alpha HX/CX$ and $\alpha HX/A$ (A: 1,2,4-trimethylbenzene) were found to be 5.5 and 0.45, respectively. Any high boiling compounds were not detected. The colour of adsorbent (white) was not changed.

EXAMPLE 3

The same procedure as in Example 1 was repeated except that 1,2,3-trimethylbenzene was used as the desorbent. $\alpha HX/CX$ and $\alpha HX/A$ (A: 1,2,3-trimethylbenzene) were found to be 5.1 and 0.37, respectively. Any high boiling compounds were not detected. The colour of adsorbent (white) was not changed.

EXAMPLE 4

The same procedure as in Example 1 was repeated except that a type Y aluminosilicate zeolite (SK-40, a product of Union Carbide; metal cation is Na+) was used as the adsorbent. $\alpha HX/CX$ and $\alpha HX/A$ (A: 1,3,5-trimethylbenzene) were found to be 26.7 and 0.60, respectively. Any high boiling compounds were not detected. The colour of adsorbent (white) was not changed.

EXAMPLE 5

The same procedure as in Example 4 was repeated except that a type Y aluminosilicate zeolite exchanged with K+ ion was used as the adsorbent. $\alpha HX/CX$ and $\alpha HX/A$ (A: 1,3,5-trimethylbenzene) were found to be 3.6 and 0.59, respectively. Any high boiling compounds were not detected. The colour of adsorbent (white) was not changed.

EXAMPLE 6

The same procedure as in Example 5 was repeated except that 1,2,3-trimethylbenzene was used as the desorbent. $\alpha HX/CX$ and $\alpha HX/A$ (A: 1,2,3-trimethylbenzene) were found to be 3.5 and 0.60, respectively. Any high boiling compounds were not detected. The colour of adsorbent (white) was not changed.

EXAMPLE 7

The same procedure as in Example 1 was repeated except that the adsorption temperature was 120° C. $\alpha HX/CX$ and $\alpha HX/A$ (A: 1,3,5-trimethylbenzene) were found to be 4.8 and 0.84, respectively. Any high boiling compounds were not detected. The colour of adsorbent (white) was not changed.

COMPARATIVE EXAMPLE 1

The same conditions as in Examples 1 and 4 were applied except that methyl alcohol, aniline, and acetone were used as the desorbent. As a result, the desorbent was mainly adsorbed on the adsorbent with cyclohexene little adsorbed thereon, so that it was substantially difficult to obtain the exact value of $\alpha HX/CX$. The value of $\alpha HX/A$ was smaller than 0.1 in all the cases.

EXAMPLE 8

In FIG. 1, the apparatus comprises three zones, (1) being a desorption zone, (2) being a rectification zone and (3) being an adsorption zone. Each zone comprises several columns, e.g. four, six, and six columns, which are charged with adsorbent. These zones are serially and circularly interconnected in order. In the desorption zone (1), cyclohexene adsorbed on an adsorbent is displaced by contact with a desorbent stream, while simultaneously removing an extract stream comprising desorbent and cyclohexene. In the rectification zone (2), the adsorbent in this zone is contacted with a reflux stream (comprising cyclohexene and desorbent) to effect a purification of cyclohexene and this stream is directed to maintain countercurrent operation against a simulated flow of the adsorbent.

In the adsorption zone (3), cyclohexene is selectively adsorbed on the adsorbent from a feed containing a mixture of cyclohexene and cyclohexane, with simultaneous making up a raffinate stream which contains the desorbent and the less selectively adsorbed components of the feed.

The individual columns are serially and circularly connected to each other by means of a relatively small diameter connecting pipe fitted with a valve, and the valve (8) which is provided between the adsorption zone and the desorption zone is closed, while simultaneously all of the other valves not shown in FIG. 1 are opened.

Additionally, all columns are connected to a desorbent feed line (4), an extract withdrawal line (5), a feed inlet line (6), and a raffinate withdrawal line (7), wherein the individual connecting embodiment is not shown in detail in FIG. 1.

In operation, the top columns of the desorption, rectification and adsorption zones are simultaneously transferred to the bottoms of the adsorption, desorption and rectification zones, respectively, at predetermined times intervals. The transfer is effected by shifting all the points of introduction and withdrawal of all the lines into and from the one column simultaneously in a downstream direction. Thus, a simulated countercurrent flow system is provided achieving an effect similar to that of a moving bed type adsorption process. Therefore, the feed containing a mixture of cyclohexene and cyclohexane may be continuously separated to produce both the selectively adsorbed component (i.e. cyclohexene) and the less selectively adsorbed component (i.e. cyclohexane), respectively.

In this Example, each adsorption column having a content volume of 19.3 cm$^3$ was charged with the sodium type, type X aluminosilicate zeolite (24–42 mesh), which was calcined for 2 hours at 450° C. before charging in columns. The valve switching interval was set about 2 minutes. A mixture of 50.4 wt. % cyclohexene and 49.6 wt. % cyclohexene was preheated to 120° C. and fed continuously through the feed inlet line (6) at a flow rate of 25 cm$^3$/hr and at a pressure of about 15 kg/cm$^2$. Furthermore, 1,3,5-trimethylbenzene was preheated to 120° C. and fed continuously through the desorbent feed line (4) at a flow rate of 516 cm$^3$/hr and at a pressure of about 25 kg/cm$^2$. An extract stream was continuously withdrawn through line (5) at a flow rate of 94 cm$^3$/hr and at a pressure of about 5 kg/cm$^2$. After 1,3,5-trimethylbenzene was removed the extract by distillation, the cyclohexene fraction had a purity of 99.1% by weight. In the raffinate stream, cyclohexene was present at less than 0.15% by weight based on the total stream.

COMPARATIVE EXAMPLE 2

The same procedure as in Example 4 was repeated except that 1-methylcyclohexene was used as the desorbent. $\alpha$HX/CX and $\alpha$HX/A (A: 1-methylcyclohexene) were found to be 15.0 and 0.99, respectively.

Some high boiling compounds (for example 1-methylcyclohexene dimers), however, were detected by gas chromatography about 6.7 wt. % in the liquid mixture. The colour of the adsorbent changed into dark brown from white.

COMPARATIVE EXAMPLE 3

The same procedure as in Example 5 was repeated except that 1-methylcyclohexene was used as the desorbent. $\alpha$HX/CX and $\alpha$HX/A (A: 1-methylcyclohexene) were found to be 7.65 and 0.88, respectively.

Some high boiling compounds, however, were detected about 0.03 wt. %. The colour of the adsorbent changed into pale brown from white.

COMPARATIVE EXAMPLE 4

The same procedure as in Example 4 was repeated except that cycloheptene was used as the desorbent. $\alpha$HX/CX and $\alpha$HX/A (A: cycloheptene) were found to be 27.3 and 1.16, respectively.

Some high boiling compounds (for example cycloheptene dimer, etc.), however, were detected about 0.5 wt. %. The colour of the adsorbent changed into grayish brown from white.

We claim:

1. A process for the separation of cyclohexene comprising the steps of: contacting a feed which contains a mixture of cyclohexene and cyclohexane with a type X aluminosilicate zeolite which contains sodium cations, whereby cyclohexene is selectively adsorbed thereon, and then contacting said zeolite which adsorbed cyclohexene with at least one trimethylbenzene, whereby cyclohexene is desorbed therefrom.

2. A process for the separation of cyclohexene comprising the steps of:
   (a) contacting a feed which contains a mixture of cyclohexene and cyclohexane with a type X aluminosilicate zeolite adsorbent which contains sodium cations, whereby a greater percentage of cyclohexene than other components of said feed is adsorbed on said adsorbent;
   (b) contacting said adsorbent with a desorbent which contains at least one trimethylbenzene, whereby cyclohexene is desorbed therefrom; and
   (c) re-using in step (a) said adsorbent which desorbed cyclohexene and adsorbed trimethylbenzene.

3. A process according to claim 1 or 2, wherein said trimethylbenzene is a member selected from the group consisting of 1,2,3-trimethylbenzene and 1,3,5-trimethylbenzene.

4. A process according to claim 3, wherein said trimethylbenzene is 1,3,5-trimethylbenzene.

5. A process according to claim 1 or 2, wherein said adsorption and desorption steps are carried out at a temperature in the range of 0° to 300° C. and at a pressure in the range of atmospheric pressure to 40 kg/cm$^2$.

6. A process according to claim 5, wherein said adsorption and desorption steps are carried out at a temperature in the range of room temperature to 200° C. and at a pressure in the range of atmospheric pressure to 30 kg/cm$^2$.

7. A process according to claim 1 or 2, wherein said zeolite contains sodium cations.

8. A process according to claim 1 or 2, wherein said zeolite contains potassium cations.

* * * * *

UNITED STATES PATENT AND TRADEMARK OFFICE
CERTIFICATE OF CORRECTION

PATENT NO. : 4,313,014
DATED : January 26, 1982
INVENTOR(S) : Tsuneyuki Kondo, et al.

It is certified that error appears in the above-identified patent and that said Letters Patent are hereby corrected as shown below:

Column 5, line 24: delete "t,0090" and insert $$-- \alpha_{HX/CX} = \frac{\left(\frac{HX \text{ adsorbed on adsorbent}}{CX \text{ adsorbed on adsorbent}}\right)}{\left(\frac{HX \text{ of liquid phase in equilibrium with adsorbed phase}}{CX \text{ of liquid phase in equilibrium with adsorbed phase}}\right)}$$

$$\alpha_{HX/A} = \frac{\left(\frac{HX \text{ adsorbed on adsorbent}}{A \text{ adsorbed on adsorbent}}\right)}{\left(\frac{HX \text{ of liquid phase in equilibrium with adsorbed phase}}{A \text{ of liquid phase in equilibrium with adsorbed phase}}\right)} --$$

Column 5, line 28: the second "cyclohexene" should be

--cyclohexane--

Column 7, line 55: "cyclohexene" should be -- cyclohexane --

Signed and Sealed this

Eighth Day of June 1982

[SEAL]

Attest:

GERALD J. MOSSINGHOFF

*Attesting Officer*     *Commissioner of Patents and Trademarks*